United States Patent
Liang (10) Patent No.: US 11,628,219 B2
(45) Date of Patent: Apr. 18, 2023

(54) SYSTEM FOR ACHIEVING HIGH-SPECIFICITY KILLING OF TARGETED CELLS AND METHOD THEREOF USING MAGNETO-ELECTRIC NANO-PARTICLES

(71) Applicant: Ping Liang, Newport Coast, CA (US)

(72) Inventor: Ping Liang, Newport Coast, CA (US)

(73) Assignee: Ping Liang, Reno, NV (US)

( * ) Notice: Subject to any disclaimer, the term of this patent is extended or adjusted under 35 U.S.C. 154(b) by 116 days.

(21) Appl. No.: 16/218,457

(22) Filed: Dec. 12, 2018

(65) Prior Publication Data

US 2019/0111136 A1   Apr. 18, 2019

Related U.S. Application Data (63) Continuation-in-part of application No. 15/326,545, filed as application No. PCT/US2015/045148 on Aug. 13, 2015, now Pat. No. 10,188,731.

(60) Provisional application No. 62/037,447, filed on Aug. 14, 2014.

(51) Int. Cl.
| | |
|---|---|
| *A61K 9/14* | (2006.01) |
| *A61K 41/00* | (2020.01) |
| *A61K 49/18* | (2006.01) |
| *A61K 9/00* | (2006.01) |
| *A61K 9/51* | (2006.01) |
| *A61N 1/32* | (2006.01) |

(52) U.S. Cl.
CPC ........ *A61K 41/0052* (2013.01); *A61K 9/0009* (2013.01); *A61K 9/0019* (2013.01); *A61K 9/5115* (2013.01); *A61K 41/0047* (2013.01); *A61K 49/1818* (2013.01); *A61N 1/327* (2013.01)

(58) Field of Classification Search
CPC .......... A61K 9/0009; A61K 9/50; A61K 9/51; A61K 9/5107; A61K 9/5115; A61K 9/5123
See application file for complete search history.

(56) References Cited

U.S. PATENT DOCUMENTS

| | | | | |
|---|---|---|---|---|
| 8,118,754 B1* | 2/2012 | Flynn | ................. | A61B 10/0233 |
| | | | | 128/897 |
| 2011/0282184 A1* | 11/2011 | Klingenbeck | ........ | G01R 33/287 |
| | | | | 600/411 |
| 2014/0197910 A1* | 7/2014 | Tolbert | ................. | H01F 1/0063 |
| | | | | 335/284 |

OTHER PUBLICATIONS

Guduru et al. (Magneto-electric Nanoparticles to Enable Field-controlled high-Specificity Drug Delivery to Eradicate Ovarian Cancer Cells; Scientific Reports; 3:2953) (Year: 2013).*

Rakesha Guduru (Bionano Electronics: Magneto-Electric Nanoparticles for Drug Delivery, Brain Stimulation and Imaging Applications, 2013, Florida International University, FIU Digital Commons, FIU Electronic These and Dissertations) (Year: 2013).*

* cited by examiner

*Primary Examiner* — Micah Paul Young (74) *Attorney, Agent, or Firm* — George Guosheng Wang; Upstream Research and Patent LLC (57) ABSTRACT

This invention provides methods and systems for achieving high-specificity killing of targeted cells using Magneto-Electric Nano-Particles (MENPs) and functional or diagnostic imaging that detects changes at the cellular level. Embodiments comprise injecting into a patient's body manufactured MENPs that have a higher tendency to accumulate near or attach to targeted cells through one or more physical forces and/or biological mechanisms; and applying a magnetic field to the MENPs to generate an action that is sufficient to cause death of the targeted cells, and using an imaging apparatus to image or detect a specific property of the MENPs or changes in a property of the MENPs due to the coupling of the MENPs with their surrounding environment.

11 Claims, 5 Drawing Sheets

SYSTEM FOR ACHIEVING HIGH-SPECIFICITY KILLING OF TARGETED CELLS AND METHOD THEREOF USING MAGNETO-ELECTRIC NANO-PARTICLES

CROSS-REFERENCE TO RELATED U.S. APPLICATIONS

This is a Continuation-in-Part application of, and claims the benefits of, U.S. application Ser. No. 15/326,545 filed on Jan. 16, 2017, which is a National Stage Entry Application of PCT/US2015/045148 filed on Aug. 13, 2015, which claims priority from U.S. Provisional Application 62/037,447 filed on Aug. 14, 2014. The entire disclosures of the above three applications are incorporated herein by reference.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

FIELD OF THE INVENTION

This invention relates generally to using magneto-electric materials to kill cancer or diseased cells and for cellular imaging, and more specifically to controlling the behavior or properties of Magneto-Electric Nano-Particles (MENPs) that penetrate into or bound to cancer cells to kill the cancer or diseased cells, and to using magneto-electric coupling of MENPs for cellular imaging.

BACKGROUND OF THE INVENTION

Like conventional magnetic nano-particles (MENPs), e.g. gadolinium- or magnetite-based, MENPs have a non-zero magnetic moment and therefore their spatial position can be remotely controlled via application of a magnetic field gradient. However, unlike MENPs, MENPs have another property, energy-efficient control of the intrinsic electric fields of MENPs by an external magnetic field. This unique capability is a result of the intrinsic magneto-electric (ME) coupling (due to the correlated magnetostrictive and piezo-electric effects) in this new class of nanostructures even at body temperature. As a result, when introduced in a biological microenvironment MENPs act as local magnetic-to-electric-field nano-converters. Consequently, MENPs are capable of distinguishing cancer cells from healthy cells by locally probing the cell membranes' electric properties, making use of the difference between the (electroporation) electrical potentials of cancer cells and healthy cells. It is known that a cancer cell's membrane porosity can be significantly increased (to allow particle and/or drug penetration through the cell membrane into cytosol) by application of a relatively high electric field (of the order of 1000 V/cm), but it takes a substantially higher field (by a factor of three or more) to achieve the same drug-penetrability effect into the healthy cells. This effect is widely known as electroporation (Cahill et al., 2010). The problem with the conventional macroscopic electroporation effect in treating cancer is the need to apply relatively high electric fields (>1000 V/cm) over a relatively large region of the body; as a result, the treatment requires relatively high energies and is accompanied with side effects because of significant energy dissipation, which in turn makes its use highly limited. Prior art creates a remote-magnetic-field-controlled electroporation effect in the vicinity of the MENPs only and therefore can enable highly selective electroporation of cancer cells at a small fraction of energy with no destructive energy dissipation when an external magnetic field of a certain range of strength is applied.

Prior art (Guduru et al. 2013) used drug-coated MENPs to carry drugs inside cancer cells to kill the cancer cells. These represent a significant advance; however, drugs are still used, which can have side effects. There is no prior art that provides mechanism for cancer cell targeting and killing mechanisms using the methods or apparatus described in this application.

EXEMPLARY EMBODIMENTS OF THE INVENTION

One aspect of the invention provides a system for achieving high-specificity killing of targeted cells. The system includes nanoparticles that have a magnetic-electric coupling property which generates an electric field when subjected to a magnetic field, and an apparatus for injecting the nanoparticles into a patient's body.

In some embodiments, the nanoparticles have a higher tendency to accumulate near or attach to targeted cells through one or more physical forces and/or biological mechanisms after been administered into a patient's body. The apparatus then includes an injection part that can apply a magnetic field to the nanoparticles that have come into sufficient proximity of, attached to or penetrated through the targeted cells' membrane to induce the nanoparticles to generate one or more disruptive actions, including an electric gradient field, an alternating electric field, and/or an alternating electric field at one or more ferromagnetic resonance frequency(ies) of the nanoparticles, which disruptive action(s) cause death of the targeted cells.

In other embodiments, the nanoparticles are Magneto-Electric Nano-Particles (MENPs) that have a magnetic-electric coupling property which generates an electric field when subjected to a magnetic field and are not loaded with a drug intended to kill targeted cells. The system then further includes an apparatus for applying a first magnetic field and a second magnetic field comprising a selector (or selecting module) to select the first magnetic field strength H with A<H<B where A and B are thresholds so that the MENPs achieve nano-electroporation to penetrate targeted cells but no or little nano-electroporation of non-targeted cells and to select the second magnetic field strength to induce the MENPs to generate one or more disruptive actions to disrupt the function of the targeted cells, including an electric gradient field, an alternating electric field, an alternating electric field at one or more ferromagnetic resonance frequency(ies) of the MENPs. The invention further provides a method for targeted killing of targeted cells using such a system. The method including (1) injecting the Magneto-Electric Nano-Particles (MENPs) into a patient's body wherein the MENPs are not loaded with a drug intended to kill targeted cells; (2) applying a first magnetic field at a level of H with A<H<B where A and B are thresholds so that the MENPs achieve nano-electroporation to penetrate targeted cells but no or little nano-electroporation of non-targeted cells, and (3) applying a second magnetic field to induce the MENPs to generate one or more disruptive actions to disrupt the function of the targeted cells, including an electric gradient field, an alternating electric field, an alternating electric field at one or more ferromagnetic resonance frequency(ies) of the MENPs.

BRIEF DESCRIPTION OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale Well-known structures and devices are shown in simplified form, omitted, or merely suggested, in order to avoid unnecessarily obscuring the present invention.

DETAILED DESCRIPTION OF THE PREFERRED EMBODIMENT

Reference may now be made to the drawings wherein like numerals refer to like parts throughout. Exemplary embodiments of the inventions may now be described. The exemplary embodiments are provided to illustrate aspects of the inventions and should not be construed as limiting the scope of the inventions. When the exemplary embodiments are described with reference to block diagrams or flowcharts, each block may represent a method step or an apparatus element for performing the method step. The invention provides the following exemplary embodiments #1-#43.

Embodiment #1

A method for achieving high-specificity killing of targeted cells comprising administering manufactured MENPs into a patient's body wherein the MENPs have a higher tendency to accumulate near or attach to targeted cells through one or more physical forces and/or biological mechanisms, after an amount of MENPs have come into sufficient proximity of, attached to or penetrated through the targeted cells' membrane, applying a magnetic field to the MENPs to generate one or more of an electric field via the MENPs, a mechanical motion, increase temperature of the MENPs, which is sufficient to cause death of the targeted cells.

Embodiment #2

The method of Embodiment #1 wherein the magnetic field being applied is an alternating field to cause an alternating electric field and/or mechanical motion to disrupt the functions of the targeted cells.

Embodiment #3

The method of Embodiment #1 wherein the said electric field and/or mechanical motion causes no harm or minimal harm to cells not targeted by the MENPs.

Embodiment #4

The method of Embodiment #1 further comprising loading one or more drugs on the MENPs to enhance the killing of the targeted cells.

Embodiment #5

The method of Embodiment #1 further comprising using MENPs that have a non-zero magnetic moment and, after the MENPs are administrated into a patient's body, applying an adequately high magnetic field gradients to remotely navigate the MENPs through the blood circulation and/or lymph systems towards a targeted site and/or away from one or more organs or areas to be avoided.

Embodiment #6

The method of Embodiment #1 wherein the MENPs are administrated via subcutaneous, intratumoral, peritumoral, intraperitoneal, or intravenous injection, or oral intake, or by other means.

Embodiment #7

The method of Embodiment #1 wherein when the MENPs are injected locally to or near a targeted site, further comprising applying an external magnet field while the MENPs are being injected to attract the MENPs at the targeted site and to cause the MENPs to penetrate the membrane of cancer cells.

Embodiment #8

The method of Embodiment #7 further comprising maintaining an external magnet field for a period of time after the injection.

Embodiment #9

The method of Embodiment #1 further comprising applying a permanent magnetic disk with desired shape, magnetic field strength and a hole in the middle to a targeted site and injecting to the targeted site using a needle that goes through the hole.

Embodiment 10

The method of Embodiment #1 further comprising applying an electromagnet with desired shape, magnetic field strength and a hole in the middle to a targeted site and injecting to the targeted site using a needle that goes through the hole.

Embodiment #11

The method of Embodiment #1 wherein the MENPs have the shape of nano-rods.

Embodiment #12

The method of Embodiment #1 further comprising applying an external magnetic gradient field to guide the MENPs towards the targeted site, wherein the external magnetic gradient field is a static field and/or a dynamic field.

Embodiment #13

The method of Embodiment #1 wherein the magnetic field is applied locally in the vicinity of a targeted site and/or globally to the entire body.

Embodiment 14

The method of Embodiment #1 wherein applying a magnetic field further comprising applying a first magnetic field locally to a targeted site and applying a second magnetic field globally to the entire body, wherein the two magnetic field is applied concurrently or sequentially.

Embodiment #15

The method of Embodiment #1 further comprising coating or conjugating the MENPs with ligands or antibodies that bind to certain receptors or other biomarkers that are specific to or over-expressed in targeted cells.

Embodiment #16

The method of Embodiment #1 wherein applying a magnetic field further comprising applying a rotating or pulsating magnetic field to generate a rotating or pulsating electric polarization on the MENPs to facilitate targeted nano-electroporation, wherein the strength and/or frequency of the rotating, or pulsating electric polarization is selected to induce selective nano-electroporation of targeted cells.

Embodiment 17

The method of Embodiment #1 wherein applying a magnetic field further comprising applying an alternating magnetic field to excite one or more ferromagnetic resonance frequencies of the MENPs to disrupt, kill or cause damages to the mechanisms of the targeted cells.

Embodiment #18

The method of Embodiment #17 further comprising giving the MENPs specific ferromagnetic resonance frequency (ies) by changing their intrinsic and/or or extrinsic properties.

Embodiment 19

The method of Embodiment #17 further comprising applying another magnetic field to control the ferromagnetic resonance frequency(ies) of the MENPs.

Embodiment #20

A system for achieving high-specificity killing of targeted cells comprising nanoparticles that generate an electric field when subjected to a magnetic field due to magnetic-electric coupling and have a higher tendency to accumulate near or attach to targeted cells through one or more physical forces and/or biological mechanisms after been administered into a patient's body; and an apparatus that can apply a magnetic field to the nanoparticles that have come into sufficient proximity of, attached to or penetrated through the targeted cells' membrane to induce the nanoparticles to generate one or more disruptive actions, including an electric gradient field, an alternating electric field, an alternating electric field at one or more ferromagnetic resonance frequency(ies) of the MENPs, heat and mechanical motion, which disruptive action(s) is sufficient to cause death of the targeted cells.

Embodiment #21

The system in Embodiment 420 further comprising nanoparticles made by first depositing a thin film with the required properties via sputter deposition, evaporation, or another deposition technique, and then using ion beam proximity lithography or imprint or other lithography methods to cut the thin films into nanoparticles of desired shapes and sizes.

Embodiment #22

The system in Embodiment #20 wherein the apparatus for applying a magnetic field to the nanoparticles uses one or more magnetic needles that are used to both inject MENPs and produce the magnetic field to keep the MENPs in the injected area, include nano-electroporation and/or disruptive actions.

Embodiment 23

The system in Embodiment #20 wherein the apparatus for applying a magnetic field to the nanoparticles uses one or more highly magnetic field conducting needles to conduct external magnetic field to a location deep inside a patient's body.

Embodiment #24

The system in Embodiment #20 wherein the apparatus for applying a magnetic field to the nanoparticles injects one or more thin magnetic wires through the hollow of an injection needle into the targeted site to produce the magnetic field to keep the MENPs in the injected area, including nano-electroporation and/or disruptive actions.

Embodiment #25

The system in Embodiment #24 wherein one end of a thin magnetic wire is kept at the end of the injecting device that is outside the body or connected to handle and the wire can be removed by pulling the wire through the injecting, needle when the treatment is completed.

Embodiment #26

The system in Embodiment #24 wherein a thin magnetic wire is self-coiling such that when it is pushed out of the needle and into the body, it will coil so that the mass of the wire will stay near the site of the injection.

Embodiment #27

The system in Embodiment #24 wherein a thin magnetic wire has a dull and smooth or spherical tip so that when it is injected, it causes minimal or no puncture of blood vessels.

Embodiment #28

A system for targeted killing of targeted cells using MENPs comprising MENPs that are to be injected into a patient's body; an apparatus for applying a second magnetic field at a level A<H<B where A and B are thresholds so that the MENPs achieve nano-electroporation to penetrate targeted cells but no or little nano-electroporation of non-targeted cells; an apparatus applying a third magnetic field to induce the MENPs to generate one or more disruptive actions to disrupt the function of the targeted cells, including an electric gradient field, an alternating electric field, an alternating electric field at one or more ferromagnetic resonance frequency(ies) of the MENPs, heat and mechanical motion.

Embodiment #29

The system of Embodiment #28 wherein the second magnetic field is applied prior to the application of the third magnetic field.

Embodiment #30

The system of Embodiment #29 wherein a sufficiently long waiting period is inserted between the application of the second magnetic field and the third magnetic field to give the body sufficient time to move most or all of the free MENPs that did not penetrate or bind to targeted cells out of the body.

Embodiment #31

The system of Embodiment #28 wherein the second magnetic field and the third magnetic field are applied concurrently.

Embodiment #32

The system of Embodiment #28 wherein an apparatus generates both the second magnetic field and the third magnetic field.

Embodiment #33

The system of Embodiment #28 wherein the apparatus for generating the second magnetic field and the third magnetic field generates a localized magnetic field for targeted site that is localized.

Embodiment #34

The system of Embodiment #28 wherein the apparatus for generating the second magnetic field and the third magnetic field generates a wide area magnetic field that covers a large body area or the whole or most part of the body to which the targeted cells have spread.

Embodiment #35

The system in Embodiment #28 wherein the strength and/or frequency of the third magnetic field is chosen to cause the MENPs that have penetrated into targeted cells to kill the targeted cells but does not cause other MENPs that still remain in the body to penetrate or harm untargeted cells.

Embodiment #36

The system in Embodiment #28 further comprising an apparatus for applying a first magnetic field externally to produce higher concentration of MENPs at and around a localized targeted site or in an organ or body part, prior to the application of the second magnetic field.

Embodiment #37

The system of Embodiment #36 wherein a single apparatus generates the first magnetic field, the second magnetic field and the third magnetic field.

Embodiment #38

The system in Embodiment #36 wherein the apparatus for generating the magnetic field further comprising a sensor or imaging device that measures one or more of the following: the strength and/or gradient of the magnetic field at one or more location, the position and/or motion of the MENPs inside the body, or effective local electric field calculated from magnetic imaging of MENPs; and a feedback control loop that uses the measurement(s) to control the generation and application of the magnetic field to achieve desired strength, frequency and/or distribution of the magnetic field.

Embodiment #39

The system in Embodiment #36 wherein the apparatus for generating the magnetic field further comprising multiple permanent or electro-magnets arranged in an enclosure to generate a 3-dimensional magnetic field with sufficient strength in tissues or organ deep inside a human body by constructively superimposing magnetic field vectors from multiple magnets at targeted locations.

Embodiment #40

The system in Embodiment #36 further comprising a magnetic imaging device that produces measurements or images of the 3D distribution of the magnetic field; and using, the measurements or images to control the generation of the 3D magnetic field to guide MENPs to the desired location inside a human body and/or to generate magnetic field at a desired location to produce nano-electroporation of targeted cells and/or generate one or more of the disruptive actions.

Embodiment #41

The system in Embodiment #36 further comprising calibrating the magnetic imaging device to establish a sufficiently accurate mapping of the measurements or images of the 3D distribution of magnetic field to actual locations inside the patient's body.

Embodiment #42

A method for functional or diagnostic imaging that detects changes at the cellular level comprising injecting MENPs in vitro into a biological sample or in vivo into a biological system; after a period of time or after the MENPs have reached a site to be imaged, using a magnetic resonance imaging apparatus to image or detect the specific magnetic resonance frequency(ies) of the MENPs or changes in the magnetic resonance frequency(ies) of the MENPs; mapping the detected or imaged specific magnetic resonance frequency(ies) of the MENPs or changes in the magnetic resonance frequency(ies) of the MENPs to the corresponding types or properties, or changes in the types or properties, of cells or bodily fluid in the immediate nano-environment of the MENPs that caused the specific magnetic resonance frequency(ies) or changes in the magnetic resonance frequency(ies) of the MENPs.

Embodiment #43

The method in Embodiment #42 further comprising a probing step by first applying an external magnetic field to generate electrical field around the MENPs to interact with the cells in the immediate nano-environment of the MENPs to detect or amplify the effect of ionic or electrical properties of different cells or changes in the properties of cells; and using a magnetic resonance imaging apparatus to image or detect the effect of the probing due to the further distinguished interactions of the MENPs with different cells.

More broadly, the present inventions provide methods, processes or construction of an apparatus for using the unique physics of MENPs to achieve high-specificity killing of cancer cells via application of an external magnetic field to generate an electric field and/or mechanical motion after one or more MENPs have penetrated the cancer cells' membrane, without loading or coating any drug on the MENPs, and causing no harm or only minimum harm to normal cells.

In both cases (drug-loaded MENPs or MENPs alone), the MENPs have a non-zero magnetic moment and therefore, if administrated in a patient's body, can be remotely navigated through the blood circulation and/or lymph systems via application of adequately high remote magnetic field gradients (e.g., >1000 Oe/cm). The MENPs can be administrated via subcutaneous (SC) intratumoral (IT), peritumoral (PT), intraperitoneal (IP), or intravenous (IV) injection, or oral intake (OI), or by other means.

In case of IT, IP or PT injection, the passive targeting is initiated externally (by injecting directly into or near the tumor). One embodiment applies an external magnet field that serves to attract the MENPs at the tumor site and/or to cause the MENPs to penetrate the membrane of cancer cells. The magnetic field can be applied either via permanent magnets or electromagnets depending on the size and shape of the tumor. The external magnetic field is applied prior to or at the time of the IT, IP or PT injection and is maintained afterwards for a period of time. The strength of the external magnetic field is chosen to be (1) sufficiently strong to overcome the viscosity of the cellular microenvironment, preventing nano-particles from moving to other parts via circulation of body fluids and further amplifying the well-known Enhanced Permeability and Retention (EPR) effect that nano-particles tend to accumulate in tumor tissue much more than they do in normal tissue, (2) sufficiently strong to cause the MENPs to penetrate the membrane of cancer cells, but (3) not too strong to cause the MENPs to penetrate the membrane of normal cells. At a second stage, after the MENPs are inside the cancer cells, one embodiment applies an external magnetic field to generate local electric fields on the MENPs via the magnetic-electric (ME) coupling characteristics of the MENPs. When the electric field is sufficiently strong, it disrupts the mechanisms of the cancer cells or kills the cancer cell by electric shock. In another embodiment, the MENPs are coated with drugs and the combination of the electric field and drug kills the cancer cells.

Figure 1:
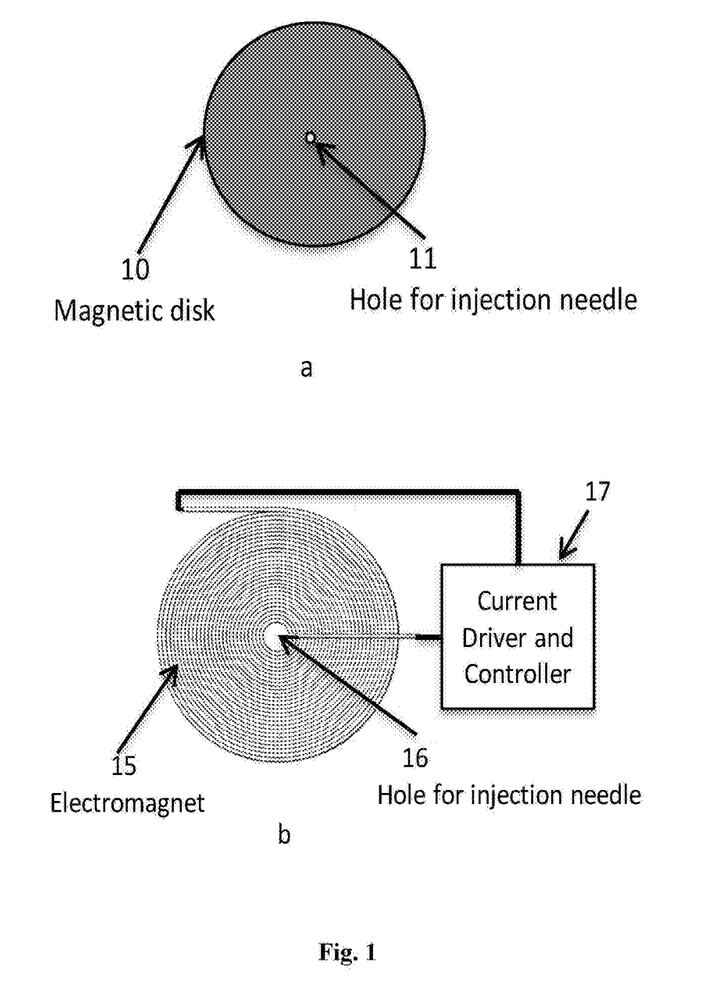
FIG. 1 shows a magnet disk and an electromagnet apparatus used to generate external magnetic field to control MENPs.

One embodiment for targeting with IT, IP or PT injection uses a permanent magnetic disk 10 with a hole 11 in the middle for the needle to go through, illustrated in FIG. 1a. The disk is first applied to the targeted site prior to or at the time of injection. The shape and magnetic field strength of the disk can be customized to the targeted site, where the required magnetic field strength is achieved by selecting the material and thickness of the disk. Another embodiment for targeting with IT, IP or PT injection uses an electromagnet 15 with a hole 16 in the middle whose size and shape is matched with the targeted site, and the required the magnetic field strength is achieved by selecting the number of windings of the coils and/or the amount and or frequency of electric current applied by a Current Driver and Controller, see FIG. 1b.

In case of IV administration (including IV injection and IV dripping using a catheter), drug-loaded MENPs and MENPs alone can also be further navigated to the tumor cells via application of magnetic field gradients. In one embodiment, MENPs that are sufficiently small (e.g., <100 nm) and have an elongated shape (e.g., elliptical, or nano-rods) are used in IV administration. We note that nano-rods propagate in the circulatory system easier than equivalent sized spheres. Such IV-administered MENPs can potentially reach every cell in the body through the body's circulatory system even without application of an external magnetic field. However, in one embodiment, an external magnetic gradient field is applied to guide the MENPs towards the cancer site to further improve the targeting capability. The external magnetic gradient field can be a static field or a dynamic field. One embodiment applies a magnetic field at a level of strength high enough to trigger the nano-electroporation effect to "drive" MENPs, with or without loaded drugs, inside the cancer cells but not high enough to affect the normal cells. This magnetic field can be applied either locally in the vicinity of the tumor or globally to the entire body. The duration of the field application ranges from hours to many days, maintained during the length of IV dripping or for a period of time after the IV injection or IV dripping, depending on the stage and type of cancer. In addition, to further improve the active targeting capability, the MENPs with or without loaded drugs, can be further conjugated with ligands or antibodies that are specific to certain surface receptors or other biomarkers which are over-expressed around the cancer cells. This causes the MENPs in the circulation to attach to cancer cells and facilitates the nano-electroporation by the externally applied magnetic field. In other words, the roles of ligands/antibodies and MENPs are complementary to each other: the ligands/antibodies enable delivery of MENPs towards the surface of cancer cells while MENPs induce the nano-electroporation to move inside cancer cells targeted by the ligands or antibodies. Both effects are specific to cancer cells and therefore the specificity of the combined effect can be significantly improved.

In another embodiment, a rotating or pulsating magnetic field is applied which generates a rotating or pulsating electric polarization on the MENPs to facilitate targeted nano-electroporation. The strength and/or frequency of the rotating or pulsating electric polarization is selected to induce selective nano-electroporation of targeted diseased cells, i.e., the strength and/or frequency rotating or pulsating of the external magnetic field is chosen such that the MENPs only or mainly penetrate the membranes of one or more types of targeted cells and do not or mostly do not penetrate the membranes of other cells. Targeted penetration of the membrane of certain types of diseased cells is better achieved using rotating or pulsating polarization of the MENPs.

In one embodiment, after MENPs have penetrated through the cancer or other diseased cell membranes through nano-electroporation, one or more of the following mechanisms is applied to kill the cancer or diseased cells:

(A). Apply an external magnetic field to generate strong enough electric field on the MENPs inside the cancer or diseased cells to kill them, e.g., local electric fields on the order of 1000 V/cm, which can be attained a few nanometers away from MENPs via the application of an external magnetic field on the order of 100 Oe;

(B). Apply an alternating external magnetic field to induce an alternating electric field on the MENPs inside the cancer or diseased cells wherein the strength and frequency of the field is selected such that it disrupts the functions of these cells, thus causes them to die off;

(C). Apply an alternating external magnetic field to generate heat on the MENPs inside the cancer or diseased cells to kill them wherein the strength and frequency of the field is selected to generate sufficient heat to kill the cancer or diseased cells without harming surrounding cells or tissues;

(D). Apply an alternating external magnetic field to induce mechanical motions of the MENPs inside the cancer or diseased cells to disrupt the cell functions or to physically damage the cells from inside, causing them to die off, where the mechanical motions may include linear motion, slicing, collisions or vibrations, or combinations thereof.

In another embodiment, a ferromagnetic resonance strongly dependent on the interaction of MENPs with its nano-environment (in the proximity of a few nanometers away from the nano-particles) is used to selectively disrupt or shut down the operation of certain cellular organelles, e.g. nucleus, microtubules, and others, when MENPs are already inside the cancer cells. The ferromagnetic resonance of MENPs depends on the saturation magnetization, which in turn, because of the ME effect, strongly depends on the electric fields that are associated with the interaction of MENPs with the nano-environment. As the nano-environment changes, so does the saturation magnetization and consequently the ferromagnetic resonance frequency(ies). This resonant frequency or set of resonant frequencies can be varied in a wide range by varying intrinsic properties, e.g. the magneto-crystalline anisotropy energy and the exchange coupling constant, or extrinsic properties, e.g. the shape-induced anisotropy energy. In addition, the resonant frequency(ies) can be controlled by application of an external DC magnetic field. By specifically selecting the resonant frequencies, certain functions of cancer cells can be shut down with a relatively high specificity on demand. For example, the microtubules responsible for cancer cell proliferation could be remotely controlled via ferromagnetic resonance of the MENPs. Namely, the resonant frequency of MENPs in the proximity (of 2 nm) of the microtubules changes because of the changes in the saturation magnetization. The saturation magnetization change is due to the ME effect caused by the interaction of the MENPs and the microtubules. An external AC magnetic field at the new modified resonant frequency can then be applied to disrupt or cause damages to, the microtubules.

Figure 2:
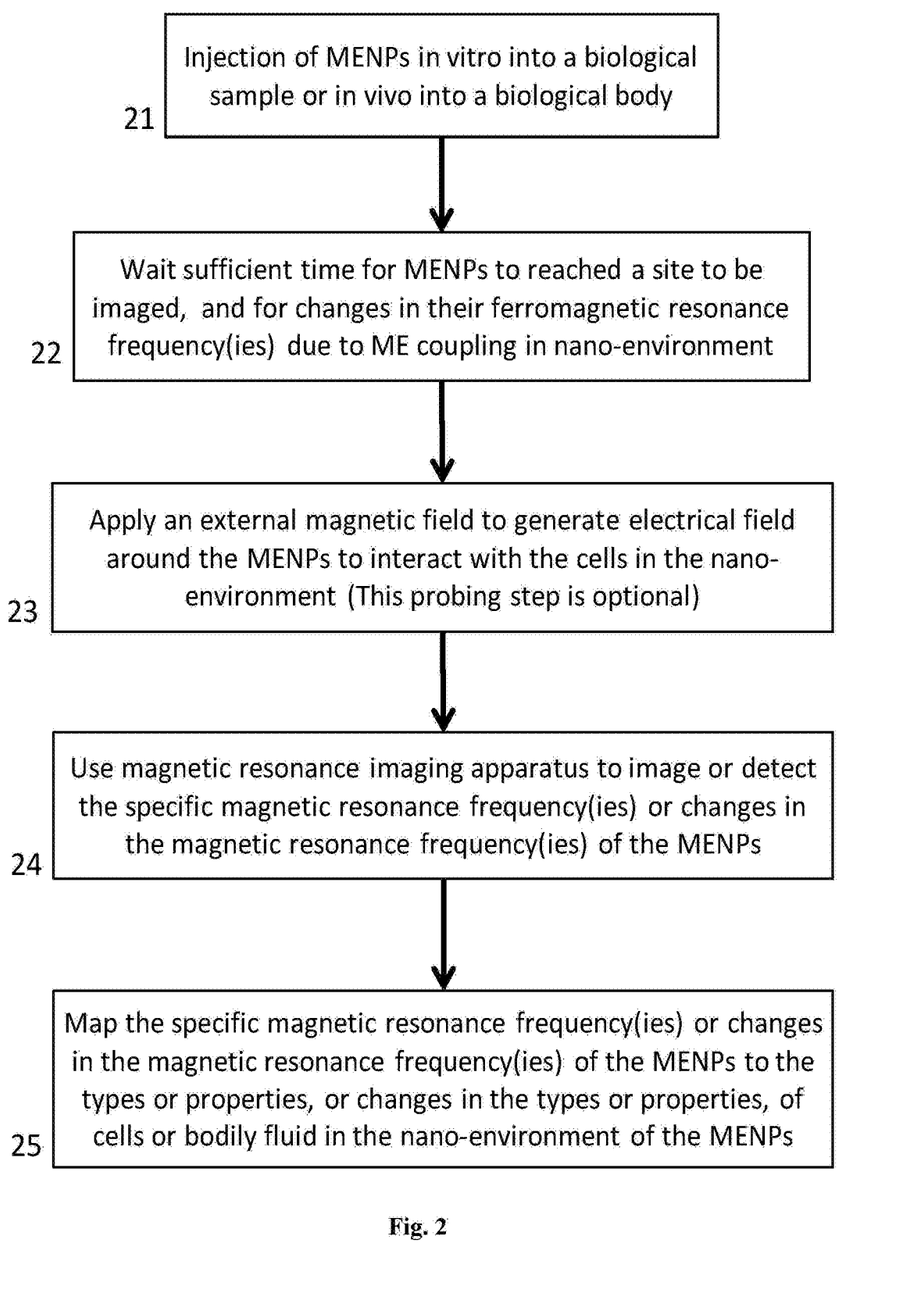
FIG. 2 is a flow chart of an embodiment of functional or diagnostic imaging method or apparatus that detects changes at the cellular level using the ME coupling of MENPs with the nano-environment.

Another embodiment is a functional or diagnostic imaging method or apparatus that detects changes at the cellular level, shown in FIG. 2. The first step 21 in FIG. 2 is the injection of MENPs in vitro into a biological sample or in vivo into a biological system, e.g., an animal or human body. In 22 in FIG. 2, after MENPs have reached a site to be imaged, because of the tight ME coupling of the MENPs, the ionic or electrical properties of different cells or bodily fluid in the immediate nano-environment of the MENPs, or in the cells to which MENPs are bound, cause different changes in the magnetic properties of the MENPs, thus their ferromagnetic resonance frequency(ies). In 24 in FIG. 2, a magnetic resonance imaging apparatus is used to image or detect the specific magnetic resonance frequency(ies) of the MENPs or changes in the magnetic resonance frequency(ies) of the MENPs. In 25 in FIG. 2, the detected or imaged specific magnetic resonance frequency(ies) of the MENPs or changes in the magnetic resonance frequency(ies) of the MENPs are then mapped to the corresponding types or properties, or changes in the types or properties, of cells or bodily fluid in the immediate nano-environment of the MENPs that caused the specific magnetic resonance frequency(ies) or changes in the magnetic resonance frequency(ies) of the MENPs. In 23 in FIG. 2, the embodiment may further include a probing step that first applies an external magnetic field to generate electrical field around the MENPs to interact with the cells in the immediate nano-environment of the MENPs to detect or amplify the effect of ionic or electrical properties of different cells or changes in the properties of cells, e.g., causing nano-electroporation into cancer cells. The interactions of the MENPs with some cells will be further distinguished from other cells. Thereafter, a magnetic resonance imaging apparatus is used to image or detect the effect of the probing due to the further distinguished interactions of the MENPs with different cells, e.g., cancer cells and normal cells.

The above mechanisms of targeted killing of cancer or diseased cells using nano-electroporated MENPs provide a new cancer treatment that is non-toxic or low-toxic. The steps of a preferred embodiment, as shown in FIG. 3, comprise:

Step 1 (31 in FIG. 3): Injecting MENPs, via IT, PT, IP, IV (IV injection or dripping using a catheter) or by other means.

Step 2 (32 in FIG. 3, optional): Applying a first magnetic field externally to produce higher concentration of MENPs at and around a diseased site or in an organ or body part. This step is optional and applicable to a disease site this is localized, e.g., the site of a tumor, and is skipped and not or less applicable when the cancer or diseased cells are widely distributed, e.g., in the circulatory system or metastasized to many sites).

Figure 3:
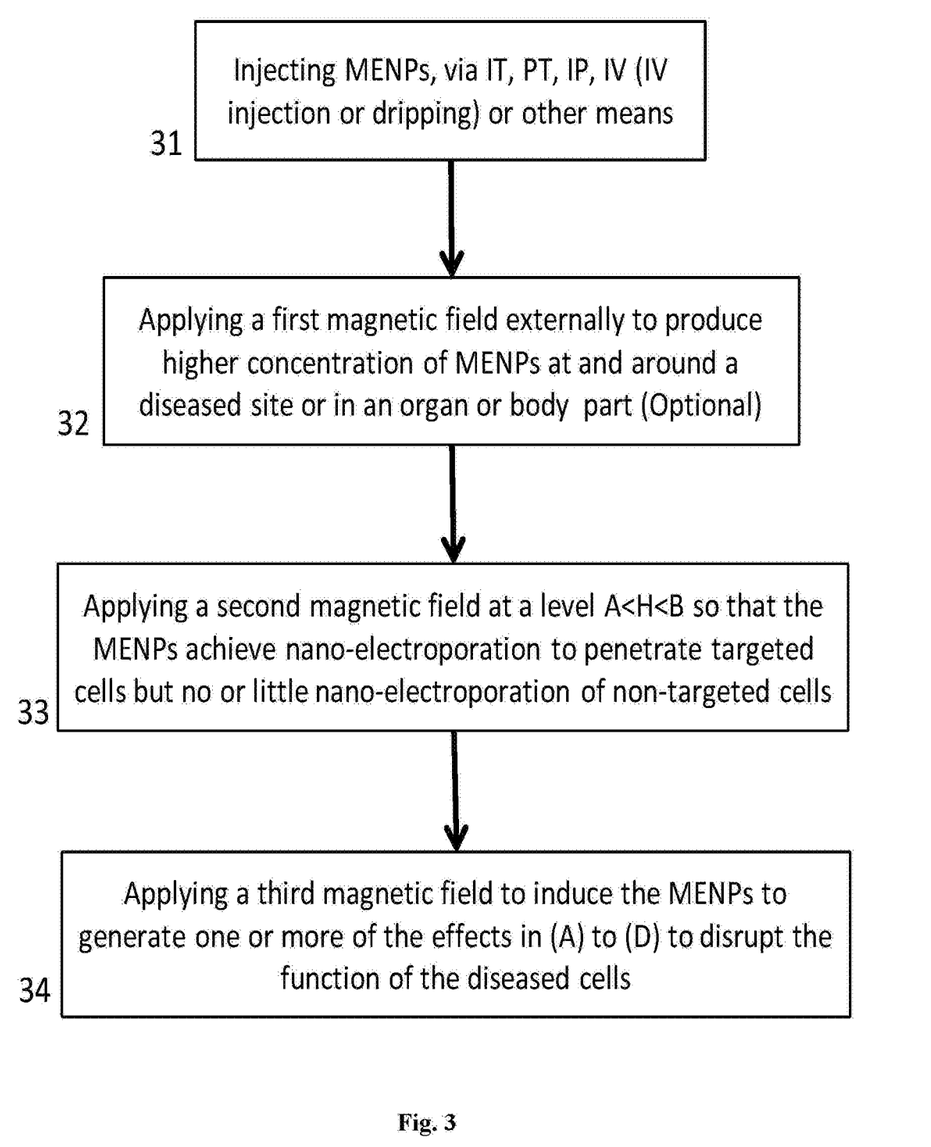
FIG. 3 is a flow chart of an embodiment for targeted killing of cancer or diseased cells using nano-electroporated MENPs that provide a new cancer treatment that is non-toxic or low-toxic.

Step 3 (33 in FIG. 3). Applying a second magnetic field at a level A<H<B where A and B are thresholds so that the MENPs achieve nano-electroporation to penetrate targeted cancer or diseased cells but no or little nano-electroporation of healthy or non-targeted cells.

Step 4 (34 in FIG. 3): Applying a third magnetic field to induce the MENPs to generate one or more of the effects in (A) to (D) listed above to disrupt the function of the diseased cells.

Steps 3 and 4 may be combined into a single step. For a disease that is localized, a localized second and/or third magnetic field this is confined to the disease site is applied. For a disease in which the targeted cells are widely distributed, a wide-area second and/or third magnetic field that covers a large body area or the whole or most part of the body is applied so that cancer or other diseased cells that are circulating, in or have metastasized to other parts of the body can be penetrated and killed.

In one embodiment, the strength and/or frequency of the third magnetic field in Step 4 is chosen to cause the MENPs that have penetrated into cancer or diseased cells to kill these targeted cells but does not cause other MENPs that still remain in the body to penetrate or harm healthy or untargeted cells. In another embodiment, a sufficiently long waiting period is inserted between Steps 3 and 4 to give the body sufficient time to excrete most or all of the free MENPs that did not penetrate or bind to cancer or diseased cells out of the body. This reduces the risk of MENPs killing healthy or untargeted cells and gives more freedom in selecting the strength and/or frequency of the third magnetic field in Step 4 to kill the diseased or cancer cells.

Because of the physical (not chemical) nature and the targeting specificity of remote-field-controlled nano-electroporation, the above embodiments can be applied to the multi-drug-resistant (MDR) cancer cell lines that are known to develop immunity to the conventional chemistry-based drugs. For the same reason, the above embodiments can be applied to eradicate isolated (i.e., not aggregated into tumors) cancer stem cells, which are difficult to eradicate using the existing chemistry-based approaches.

Shape, size, ME coupling and other properties are important for the embodiments of this invention. One embodiment for making MENPs with a wide range of properties comprises first depositing a thin film with the required properties via sputter deposition, evaporation, or another deposition technique, and then using ion beam proximity lithography (IBL) or imprint or another advanced lithography to "cut" the thin films into MENPs of desired shapes and sizes.

Figure 4:
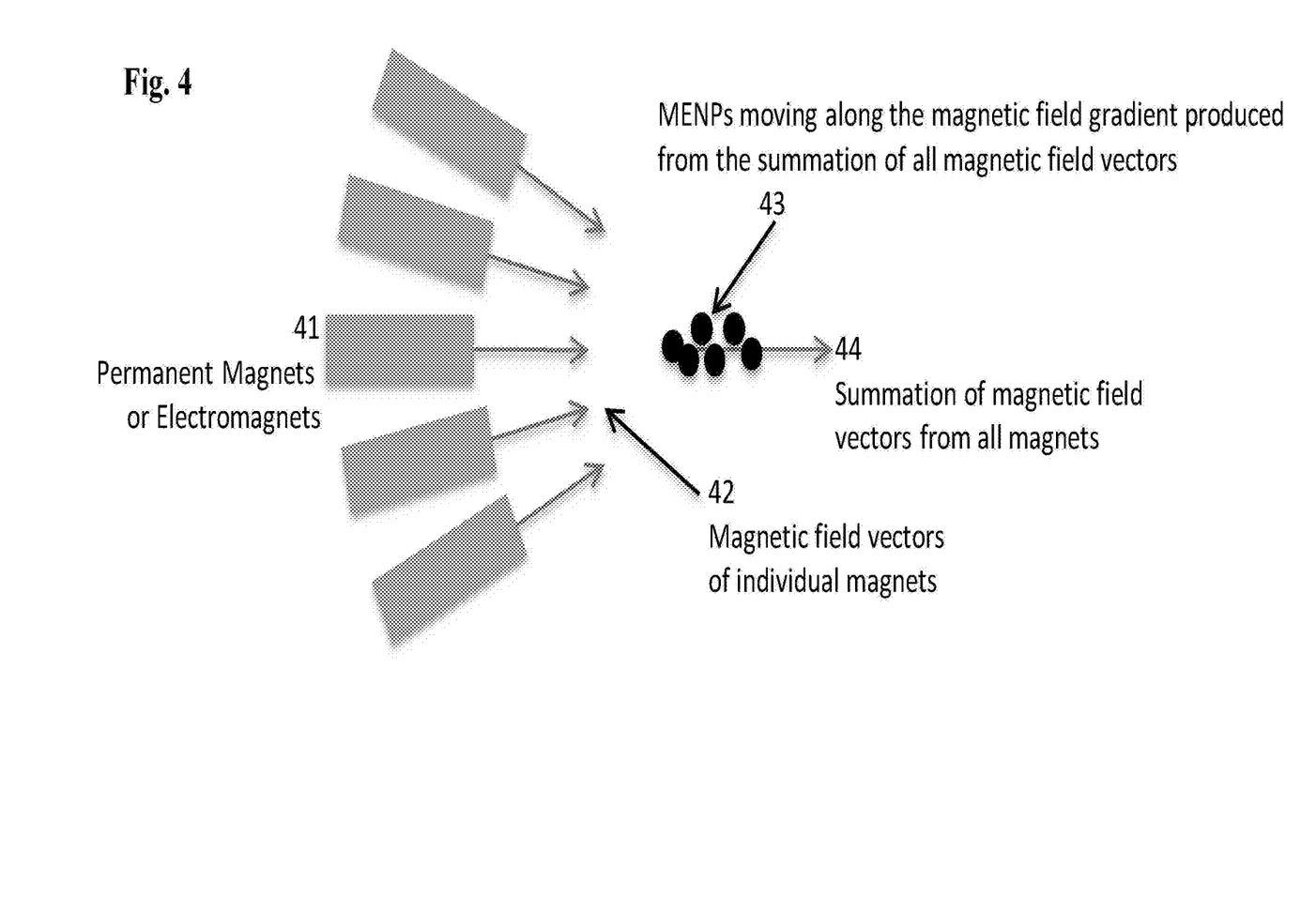
FIG. 4 illustrates the constructive superimposition of magnetic field vectors from multiple magnets at targeted locations inside a patient's body that is sufficient to move MENPs along the superimposed magnetic field gradient or to cause nano-electroporation or killing at the focus point but not elsewhere.

One embodiment is an apparatus that is capable of generating one or more of the first, second and third magnetic fields described above. This embodiment may further include a sensor or imaging device that measures one or more of the following: the strength and/or gradient of the magnetic field at one or more location, the position and/or motion of the MENPs inside the body, or effective local electric field calculated from magnetic imaging of MENPs; and provide the measurements to a feedback control loop which controls the generation and application of the magnetic field to achieve desired strength, frequency and/or distribution of the magnetic field. Yet another embodiment is an apparatus comprising multiple magnets 41 arranged in an enclosure to generate a 3-dimensional magnetic field with sufficient strength in tissues or organ deep inside a human body. The apparatus works by constructively superimposing magnetic field vectors 42 from multiple magnets 41 at targeted locations inside a patient's body, as illustrated in FIG. 4. This allows magnetic field strength sufficiently strong to attract MENPs or MNPs 43, cause them to move along the magnetic field gradient produced from the summation 44 of magnetic field vectors from all the magnets, to cause selective nano-electroporation of cancer cell, and/or to generate one or more of the cancer cell killing mechanisms in (A) to (D), at the targeted location but not strong enough at other locations to cause undesired effects on MENPs that may be still be present at other parts of the body. The magnets can be permanent magnets and/or electromagnets. In the case of permanent magnets, they can be physically moved to produce changing magnetic field gradients to guide MENPs to a location inside a human body. In the case of electromagnets, they can be electrically controlled, by selectively turning on or off, up or down, or changing the frequencies of the electric currents driving the electromagnets. The apparatus may further include a Magnetic Resonance Imaging (MRI) or a Magnetic Nano-particle Imaging (MNI) device that produces measurements or images of the 3D distribution of the magnetic field in real time or near real time, and use the measurements to control the generation of the 3D magnetic field to guide MENPs to the desired location inside a human body and/or to generate magnetic field at a desired location to produce nano-electroporation of diseased or cancer cells and/or elicit one or more of the mechanisms in (A) to (D) to kill the diseased or cancer cells. In one embodiment, the MENPs are made with adequately high magnetization value (above 10 emu/cc) to facilitate. MNI.

A calibration procedure is performed first when it is applied to a patient at a fixed position to achieve sufficiently accurate mapping of the measurements or images of the 3D distribution of magnetic field to actual locations inside the patient's body. In one embodiment, the calibration procedure establishes a common coordinate system and all measurement points and points inside a human body are mapped into points in this common coordinate system. With accurate MRI or MNI and calibration, this apparatus can achieve "pinpoint" accuracy in killing diseased or cancer cells in the desired location inside a patient's body.

Figure 5:
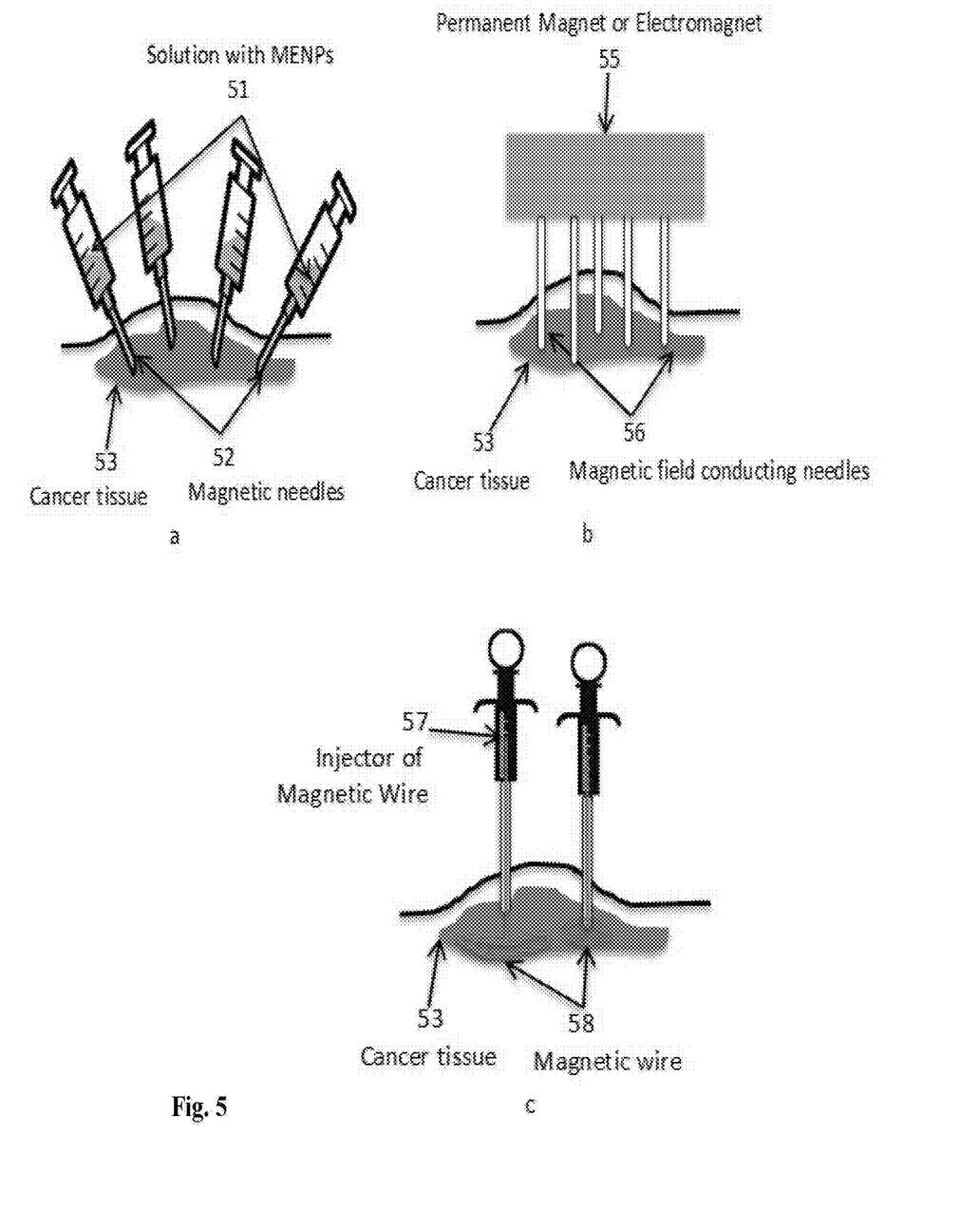
FIG. 5 shows embodiment of (a) magnetic needles, (b) magnetic field conducting needles and (c) magnetic wires for applying magnetic field deep inside tissues with high accuracy.

Another embodiment for "pinpoint" accuracy uses one or more magnetic needles 52 that is used to both inject solutions with MENPs 51 and produce the magnetic field to keep the MENPs in the injected cancer tissue area 53 and for nano-electroporation and cancer cell killing mechanisms, as shown in panel a of FIG. 5. Another embodiment uses one or more highly magnetic field conducting needles 56 to conduct external magnetic field to a location deep inside a patient's body 53, as shown in panel b of FIG. 5. In both cases, multiple needles can be used to generate a magnetic field to cover the volume of the targeted tumor 53. Yet, another embodiment injects or pushes one or more very thin magnetic wires 58 through the hollow of the injection needle of an injecting device 57 into the targeted site 53 to produce sufficient magnetic field at the targeted site for nano-electroporation and cancer cell killing mechanisms. One end of the magnetic wire is kept at the end of the injecting device 57 that is outside the body or connected to handle and the wire can be removed by pulling the wire through the injecting needle when the treatment is completed, as shown in panel c of FIG. 5. The magnetic wire may further be self-coiling such that when it is pushed out of the needle and into the body, it will coil so that the mass of the wire will stay near the site of the injection, as shown in panel c of FIG. 5. Furthermore, the wire may have a dull and smooth or spherical tip so that when it is injected, it causes minimal or no puncture of blood vessels. In all three embodiments as illustrated in FIG. 5, multiple needles or magnetic wires can be inserted into different depth and locations in a targeted volume.

Another embodiment uses one or more of the various "pinpoint" embodiments described above, including projection of magnetic field into a site inside the body, using needles or wires, as an initiation to amalgamate MENPs to a site targeted by the "pinpoint." The "pinpoint" method attracts MENPs nearby to the site and/or causes nano-electroporation of MENPs into cancer cells at the site. These MENPs are no longer mobile and further attract other passing by MENPs to the site, forming a positive-feedback self-amalgamation process. A "pinpoint" method is used to plant a "seed" for the self-amalgamation process that attracts more and more MENPs to the targeted site. The self-amalgamation process can also start without applying a "pinpoint" method at sites where nano-electroporation of cancer cells occurs under a broad magnetic field. Once nano-electroporation of cancer cell occurs, the MENPs that entered into the cancer cells can no longer move away and their presence at the site automatically attract other MENPs nearby or passing by, starting a self-amalgamation process.

Although the foregoing descriptions of the preferred embodiments of the present inventions have shown, described, or illustrated the fundamental novel features or principles of the inventions, it is understood that various omissions, substitutions, and changes in the form of the detail of the methods, elements or apparatuses as illustrated, as well as the uses thereof, may be made by those skilled in the art without departing from the spirit of the present inventions. Hence, the scope of the present inventions should not be limited to the foregoing descriptions. Rather, the principles of the inventions may be applied to a wide range of methods, systems, and apparatuses, to achieve the advantages described herein and to achieve other advantages or to satisfy other objectives as well.

The invention claimed is:

1. A system for achieving high-specificity killing of targeted cells comprising:
    Magneto-Electric Nano-Particles (MENPs), wherein the MENPs are not loaded with a drug intended to kill targeted cells,
    an apparatus for injecting the MENPs into a patient's body, and
    an apparatus for applying a magnetic field to the MENPs, to generate an electric field on the MENPs through their magneto-electric coupling property due to correlated magnetostrictive and piezoelectric effects of the MENPs;
    wherein said apparatus for applying a magnetic field to the MENPs is an apparatus for applying a first magnetic field and a second magnetic field comprising a selector (or selecting module) to select the first magnetic field strength H with A<H<B where A and B are thresholds so that the MENPs achieve nano-electroporation to penetrate targeted cells but no or little nano-electroporation of non-targeted cells and to select the second magnetic field strength to induce the MENPs to generate one or more disruptive actions to disrupt the function of the targeted cells, including an electric gradient field, an alternating electric field, an alternating electric field at one or more ferromagnetic resonance frequency(ies) of the MENPs.

2. A method for targeted killing of targeted cells using the system of claim 1, comprising
    injecting the Magneto-Electric Nano-Particles (MENPs) into a patient's body wherein the MENPs are not loaded with a drug intended to kill targeted cells;
    applying a first magnetic field at a level of H with A<H<B where A and B are thresholds so that the MENPs achieve nano-electroporation to penetrate targeted cells but no or little nano-electroporation of non-targeted cells; and
    applying a second magnetic field to induce the MENPs to generate one or more disruptive actions to disrupt the function of the targeted cells, including an electric gradient field, an alternating electric field, an alternating electric field at one or more ferromagnetic resonance frequency(ies) of the MENPs.

3. The method of claim 2, wherein the first magnetic field is applied prior to the application of the second magnetic field, or wherein the first magnetic field and the second magnetic field are applied concurrently.

4. The method of claim 2, wherein a sufficiently long waiting period is inserted between the application of the first magnetic field and the second magnetic field to give the body sufficient time to move most or all of the free MENPs that did not penetrate or bind to targeted cells out of the body.

5. The method of claim 2, wherein the strength and/or frequency of the second magnetic field is chosen to cause the MENPs that have penetrated into targeted cells to kill the targeted cells but does not cause other MENPs that still remain in the body to penetrate or harm untargeted cells.

6. The method of claim 2, further comprising applying another magnetic field externally to produce higher concentration of MENPs at and around a localized targeted site or in an organ or body part, prior to the application of the first magnetic field.

7. The method of claim 6, wherein a single apparatus is used to generate the first magnetic field, the second magnetic field and the third magnetic field.

8. The method of claim 2, further comprising
    using a sensor or imaging device to measure one or more of the following: the strength and/or gradient of the magnetic field at one or more location, the position and/or motion of the MENPs inside the body, or effective local electric field calculated from magnetic imaging of MENPs; and
    using a feedback control loop that uses the measurement(s) to control the generation and application of the first and/or second magnetic field to achieve desired strength, frequency and/or distribution of the magnetic field.

9. The method of claim 2, further comprising
    using multiple permanent or electro-magnets arranged in an enclosure to generate a 3-dimensional magnetic field with sufficient strength in tissues or organ deep inside a human body by constructively superimposing magnetic field vectors from multiple magnets at targeted locations.

10. The method of claim 6, further comprising
    using a magnetic imaging device that produces measurements or images of the 3D distribution of the magnetic field; and
    using the measurements or images to control the generation of the 3D magnetic field to guide MENPs to the desired location inside a human body and/or to generate magnetic field at a desired location to produce nano-electroporation of targeted cells and/or generate one or more of the disruptive actions.

11. The method of claim 10, further comprising calibrating the magnetic imaging device to establish a sufficiently accurate mapping of the measurements or images of the 3D distribution of magnetic field to actual locations inside the patient's body.

* * * * *